(12) United States Patent
Guo

(10) Patent No.: US 11,986,427 B2
(45) Date of Patent: May 21, 2024

(54) MULTIFUNCTIONAL EXERCISE CHAIR FOR BODY STRETCHING

(71) Applicant: Baoye Guo, Shandong (CN)

(72) Inventor: Baoye Guo, Shandong (CN)

(*) Notice: Subject to any disclaimer, the term of this patent is extended or adjusted under 35 U.S.C. 154(b) by 568 days.

(21) Appl. No.: 17/285,939

(22) PCT Filed: Mar. 29, 2021

(86) PCT No.: PCT/CN2021/083564
§ 371 (c)(1),
(2) Date: Apr. 16, 2021

(87) PCT Pub. No.: WO2021/258800
PCT Pub. Date: Dec. 30, 2021

(65) Prior Publication Data
US 2022/0331177 A1   Oct. 20, 2022

(30) Foreign Application Priority Data
Jun. 23, 2020   (CN) .......................... 202021188979.7

(51) Int. Cl.
*A61G 5/02*   (2006.01)
*A61G 5/10*   (2006.01)
(Continued)

(52) U.S. Cl.
CPC .............. *A61G 5/026* (2013.01); *A61G 5/10* (2013.01); *A61H 1/0214* (2013.01);
(Continued)

(58) Field of Classification Search
CPC ......... A61G 5/026; A61G 5/10; A61H 1/0214
See application file for complete search history.

(56) References Cited

U.S. PATENT DOCUMENTS 4,274,651 A * 6/1981 Dumont ................... B62M 1/14
280/250
4,572,501 A * 2/1986 Durham ............... A63B 22/001
601/36
(Continued)

FOREIGN PATENT DOCUMENTS

CN            2754603 Y   *  2/2006
CN          205287412 U   *  6/2016
CN          209899826 U   *  1/2020

*Primary Examiner* — Jacob D Knutson
(74) *Attorney, Agent, or Firm* — Li & Cai Intellectual Property (USA) Office

(57) ABSTRACT

Disclosed is a multifunctional exercise chair for body stretching, comprising a wheelchair frame body, wherein a mounting frame is detachably mounted on an end of the wheelchair frame body away from the driving rear wheel and located under the seat cushion, a pedal gear is rotatably mounted at a bottom of the mounting frame and a pedal is provided thereon, a hand crank gear is rotatably mounted on a top of the mounting frame and a hand crank handle is provided thereon, a rotating shaft is provided between two driving rear wheels; a driven gear is fixedly mounted on the rotating shaft, a supporting chain gear is mounted on the mounting frame and arranged adjacent to the pedal gear, and the hand crank gear, the pedal gear, the driven gear and the supporting chain gear are wound and connected by a transmission chain.

7 Claims, 2 Drawing Sheets

(51) Int. Cl.
*A61H 1/02* (2006.01)
*A63B 21/00* (2006.01)
*A63B 23/00* (2006.01)

(52) U.S. Cl.
CPC ...... *A63B 21/4034* (2015.10); *A63B 21/4035* (2015.10); *A63B 2023/006* (2013.01)

(56) References Cited

U.S. PATENT DOCUMENTS

| | | | | |
|---|---|---|---|---|
| 4,824,132 A * | 4/1989 | Moore | ............... | A61G 5/10 |
| | | | | 280/250.1 |
| 5,280,937 A * | 1/1994 | Needham | ............ | A61G 5/1051 |
| | | | | 280/270 |
| 5,651,422 A * | 7/1997 | Casali | ............... | B62B 5/0026 |
| | | | | 180/907 |
| 5,683,321 A * | 11/1997 | Barnett | ............... | B62M 1/28 |
| | | | | 280/250 |
| 6,234,504 B1 * | 5/2001 | Taylor | ............... | A61G 5/023 |
| | | | | 280/DIG. 10 |
| 9,387,139 B2 * | 7/2016 | Chang | ............... | A61G 5/026 |
| 9,452,316 B2 * | 9/2016 | Wu | ............ | A63B 23/03516 |
| 9,867,746 B2 * | 1/2018 | Chiang | ............ | A61G 5/026 |
| 2008/0246246 A1 * | 10/2008 | Dix | ............... | A61G 5/1054 |
| | | | | 280/233 |
| 2009/0020979 A1 * | 1/2009 | Genda | ............... | B62M 1/28 |
| | | | | 280/255 |
| 2014/0110978 A1 * | 4/2014 | Schneider | ............ | A61G 5/1081 |
| | | | | 297/452.42 |

\* cited by examiner

MULTIFUNCTIONAL EXERCISE CHAIR FOR BODY STRETCHING

FIELD OF THE DISCLOSURE

The present disclosure relates to the technical field of medical equipment, in particular, to a multifunctional exercise chair for body stretching.

BACKGROUND OF THE DISCLOSURE

"Rejuvenation" means restoring the body's instincts so that human can better adapt to life, improve health, delay aging, and prevent the loss of activity functions. Muscles have the function of connecting and executing body functions. Without muscles, motions cannot be completed through nerves, nor can they drive bones. Muscles also protect the bones, and reduce the impact of hits and collisions on the bones. Young people can exercise by going to the gym, but for some physically handicapped people and people with limited mobility, they can only stay on a wheelchair or lay on bed for a long time, and there is a serious lack of exercise. Exercise is especially important for this group of people. To reduce functional regression and prevent long-term sickness in bed, it is necessary to adhere to the rehabilitation training of activities of daily living in order to restore people's ability of daily living and self-care ability.

As an important mobile tool for the wounded, sick, and disabled at home for rehabilitation, turnover transportation, medical visits and outing activities, wheelchairs not only meet the mobility of physically disabled and people with mobility impairments, but more importantly, it is convenient for family members to move and take care of the sick. However, the current wheelchairs have a single function and do not have the function of facilitating rehabilitation exercises for users. Although they have a transportation function for the physically disabled and people with mobility impairments, people who use wheelchairs for a long time lack exercises for their limbs and lack of exercise, which is extremely unfavorable for rehabilitation and can easily lead to symptoms such as muscle atrophy and fatigue and also cause the deterioration of other body functions and disability.

The Chinese invention patent with the patent number CN201910277129.X discloses a multifunctional wheelchair with restoration function, including a wheelchair frame body. The wheelchair frame body is equipped with driving wheels, steering wheels, a seat cushion, a backrest and a hand-pushing armrest. A vertical rod is fixedly mounted on the wheelchair frame body and set against the backrest, and an elastic rod is detachably mounted on a top of the vertical rod. Both ends of the elastic rod are equipped with a handle, and a horizontal rod is also fixedly mounted on the vertical rod. A fixed turntable is correspondingly mounted at both ends of the horizontal rod, a moving turntable is rotatably mounted on the fixed turntable, a torsion spring is sleeved between the moving turntable and the fixed turntable, and an arm rod is fixedly mounted on the moving turntable. The invention has multiple functions, and while embodying the function of walking for the physically disabled and the disabled, it is convenient for the user to exercise the muscles and joints from the upper limbs to the lower limbs on the wheelchair. Through rehabilitation exercises, the deterioration of body functions can be effectively avoided and the rehabilitation effect is greatly improved. Although the multifunctional chair with the above structure is convenient for the user to perform rehabilitation exercises, the movement of the wheelchair is still embodies by the push of others or the user rolling the rear wheel of the wheelchair, and the combination of exercise and driving walking cannot be embodied. In addition, it does not have the function of massaging the user's back, waist, buttocks and legs, nor can it embody the user's vital signs detection and iontophoresis physiotherapy and treatment functions. For some elderly people or users with reduced respiratory system function, it is often unable to exercise for a long time, and the amount of exercise does not meet the recovery needs, which directly affects the rehabilitation effect.

Therefore, the development of a multifunctional exercise chair for body stretching not only has urgent research value, but also has good economic benefits and industrial application potential. This is the motivation and basis for the completion of the present disclosure.

SUMMARY OF THE DISCLOSURE

In order to overcome the above-mentioned defects of the prior art, the inventor has conducted in-depth research on this, and after paying a lot of creative work, the present disclosure has been completed.

Specifically, the technical problem to be solved by the present disclosure is to provide a multifunctional exercise chair for body stretching, so as to solve the problem that the current rehabilitation exercise chair cannot embody the combination of exercise and driving and does not have massage, iontophoresis physiotherapy and therapeutic function, thus lacking of auxiliary exercise technology for the elderly or users with reduced respiratory system function.

In order to solve the above technical problems, the technical solution of the present disclosure is as follows.

A multifunctional exercise chair for body stretching is provided, comprising a wheelchair frame body on which driving rear wheels, steering front wheels, a seat cushion, a backrest and a hand-pushing armrest are mounted, wherein a mounting frame is detachably mounted on an end of the wheelchair frame body away from the driving rear wheel and located under the seat cushion, a pedal gear is rotatably mounted at a bottom of the mounting frame and a pedal is provided on the pedal gear, and a hand crank gear is rotatably mounted on a top of the mounting frame and a hand crank handle is provided on the hand crank gear; a rotating shaft provided between two driving rear wheels and rotatably mounted on the wheelchair frame body, two driving rear wheels fixedly mounted on both ends of the rotating shaft, respectively, and a driven gear fixedly mounted on the rotating shaft; a supporting chain gear rotatably mounted on the mounting frame and arranged adjacent to the pedal gear; and the hand crank gear, the pedal gear, the driven gear and the supporting chain gear wound by a transmission chain, the transmission chain arranged in mesh with the hand crank gear, the pedal gear, the driven gear, and a steering gear, and the hand crank gear, the pedal gear, the driven gear and the supporting chain gear connected by the transmission chain.

As an improved technical solution, a protective shell is also fixedly mounted on the mounting frame and arranged to cover the hand crank gear, the pedal gear and the supporting chain gear.

As an improved technical solution, the seat cushion and the backrest are provided with a massage cushion and the massage cushion is located below surface layers of the seat cushion and the backrest.

As an improved technical solution, an iontophoresis instrument is fixedly mounted on a back of the backrest, and an electrode plate connected to the iontophoresis instrument is detachably mounted on a leaning surface of the backrest; and the leaning surface of the backrest is further equipped with a medicine bag for containing medicine packets, and the medicine bag is arranged corresponding to the electrode plate.

As an improved technical solution, the electrode plate is fixedly mounted on the backrest through Velcro.

As an improved technical solution, the medicine bag is a hollow mesh bag.

As an improved technical solution, a vital signs detector is further fixedly mounted on the back of the backrest and connected with an electrode sheet.

As an improved technical solution, an oxygen generator is fixedly mounted at a bottom of the seat cushion.

As an improved technical solution, a receiving box is arranged on one of hand-pushing armrests of the wheelchair frame body, and a display screen is arranged on the other one of the hand-pushing armrests.

After adopting the above technical solution, the beneficial effects of the present disclosure are as follows.

(1) The multifunctional exercise chair for body stretching is equipped with exercise function while embodying the transportation function for the physically disabled and people with mobility impairments, which is convenient for the user to perform rehabilitation exercises, so as to avoid physical function degradation and resume daily life and the purpose of self-care ability, and at the same time exercise the hands and feet through the hand crank handle and pedal, thereby embodying the driving of the wheelchair and autonomous walking.

(2) The protective shell provided on the mounting frame plays a protective role for the user, prevents the user from being scratched by gears and chains and getting clothes dirty during exercise, and at the same time, it also embodies the protection of all gears and chains. The entry of dust and impurities is effectively avoided, the service life is greatly extended, and the appearance of the wheelchair is more beautiful.

(3) The provided massage cushion has the function of physiotherapy and massage on the user's back, waist, buttocks and thighs. The physiotherapy massage provided by the massage cushion can promote blood circulation and unblocked channels and collaterals, thereby greatly improving the effect of the user's rehabilitation exercise.

(4) The iontophoresis is equipped. When using, the required medicine packet is put into the medicine bag. Under the action of the iontophoresis, the electrode plate and the medicine packet are combined to generate a directional driving force on the medicine ions, so that the effective ingredients in the medicine can penetrate the skin and mucous membranes and quickly enter the human body, acting on the user to embody the physical therapy and treatment functions of the user's treatment place, which is more conducive to the user's rehabilitation effect.

(5) The structure in which the electrode plate is mounted on the backrest by Velcro is convenient for disassembly and assembly, easy for maintenance and replacement, and can embody the fine adjustment of the installation position. The hollow mesh bag-type medicine bag is convenient for taking and placing of the medicine packet, which is more convenient for the medicine packet to act on the user, and the treatment effect is better.

(6) A vital signs detector is provided to facilitate the detection of the user's vital signs such as blood pressure, blood lipids, blood sugar, etc., so as to achieve effective monitoring of the user's vital signs, thereby helping to adjust the signs of exceeding the standard in time. The electrode sheet is attached to the user's temples and other acupuncture points, and also has physical therapy, prevention and treatment of cerebrovascular diseases.

(7) The oxygen concentrator is equipped with an independent oxygen inhalation tube and mask, which is convenient for users with impaired respiratory system to inhale at any time, especially during exercise, which has a great help effect for the elderly and users with impaired respiratory system and can reduce the difficulty of exercise for users, thereby satisfying the needs of the elderly and users with impaired respiratory system to exercise, achieve the required amount of exercise, and achieve better rehabilitation effects.

(8) The display screen on the hand-pushing armrest can display the user's health information, which is convenient for the user to understand the health information. The exercise plan displayed on the display screen is also more convenient for the user to carry out the corresponding rehabilitation projects in a reasonable and planned manner. The exercise is convenient and practical.

BRIEF DESCRIPTION OF THE DRAWINGS

In order to explain the specific embodiments of the present disclosure or the technical solutions in the prior art more clearly, the following will briefly introduce the drawings that need to be used in the description of the specific embodiments or the prior art. In all the drawings, similar elements or parts are generally identified by similar reference numerals. In the drawings, each element or part is not necessarily drawn according to actual scale.

Figure 1:
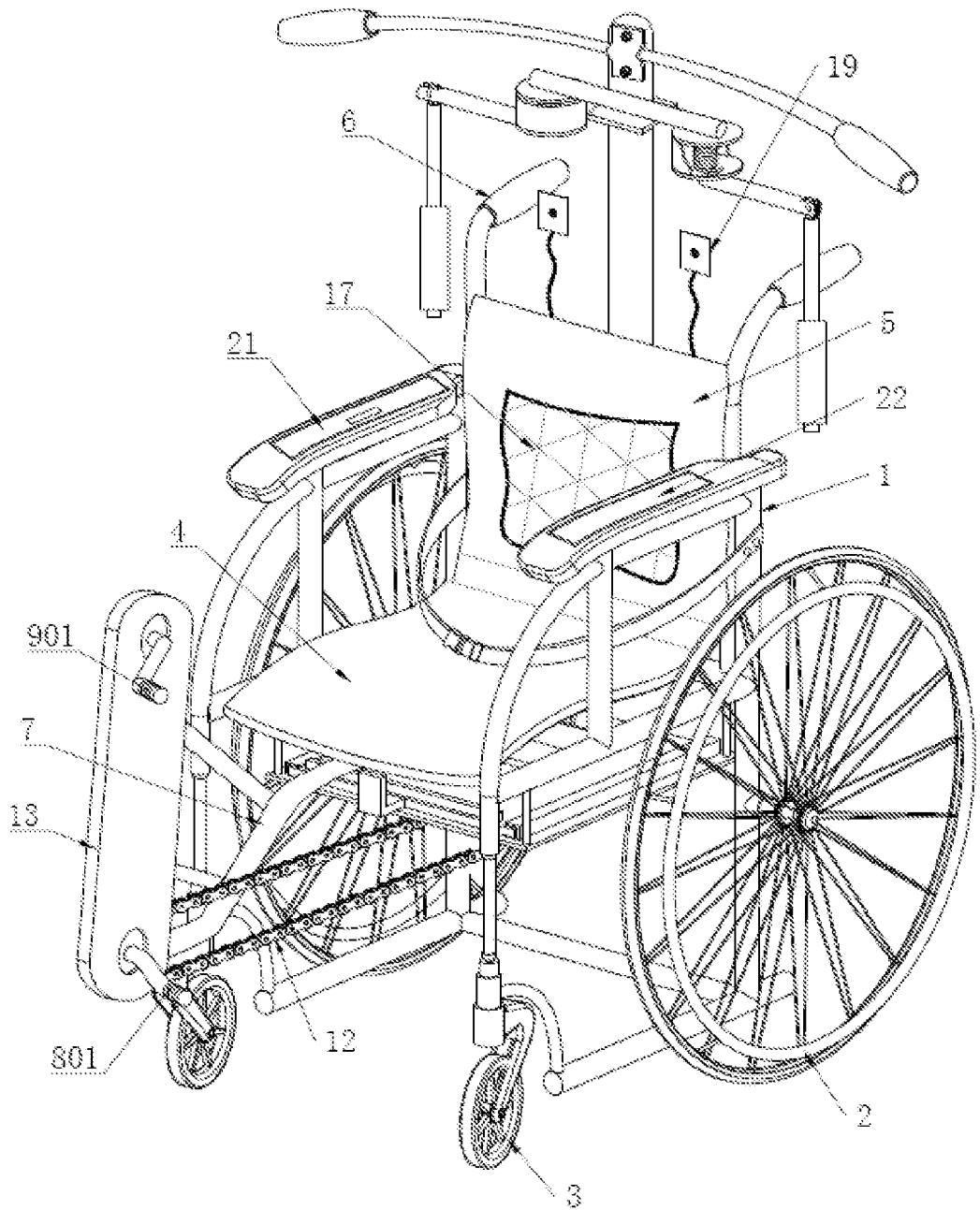
FIG. 1 is a schematic diagram of the structure of the present disclosure

Reference numeral: 1. wheelchair frame body; 2. driving rear wheel; 3. steering front wheel; 4. seat cushion; 5. backrest; 6. hand-pushing armrest; 7. mounting frame; 8. pedal gear; 801. pedal; 9. hand crank gear; 901. hand crank handle; 10. driven gear; 11. supporting chain gear; 12. transmission chain; 13. protective shell; 14. massage cushion; 15. iontophoresis instrument; 16. electrode plate; 17. medicine bag; 18. vital signs detector; 19. electrode sheet; 20. oxygen generator; 21. receiving box; 22. display screen.

DETAILED DESCRIPTION OF THE EXEMPLARY EMBODIMENTS

The present disclosure will be further described below in conjunction with specific embodiments. However, the use and purpose of these exemplary embodiments are only for exemplifying the present disclosure, and do not constitute any limitation to the actual protection scope of the present disclosure in any form, let alone limiting the protection scope of the present disclosure.

Figure 2:
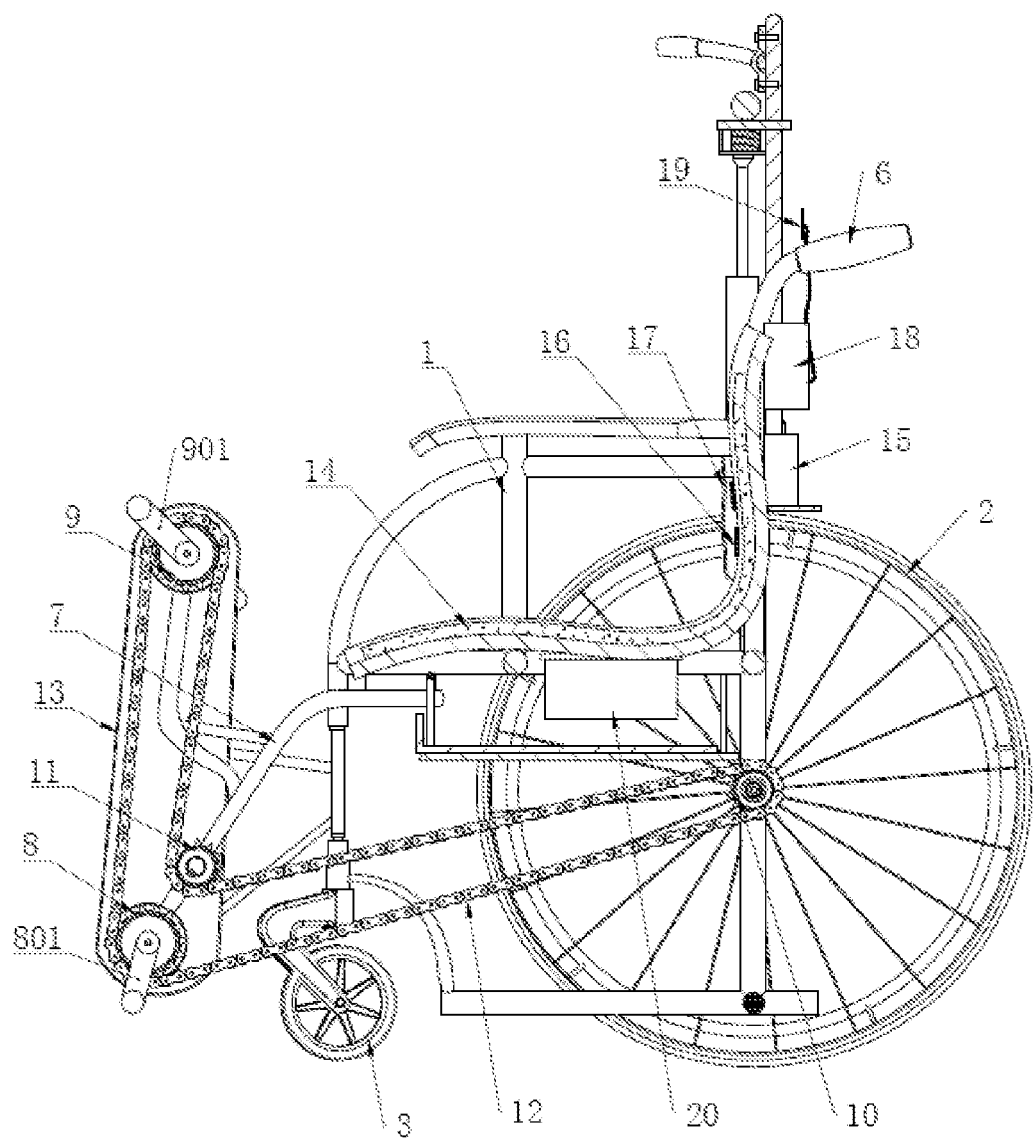
FIG. 2 is a schematic sectional view of the structure of the present disclosure.

As shown in FIG. 1 and FIG. 2, a multifunctional exercise chair for body stretching is provided, comprising a wheelchair frame body 1. The wheelchair frame body 1 is equipped with a driving rear wheel 2, a steering front wheel 3, a seat cushion 4, a backrest 5 and a hand-pushing armrest 6 thereon. A mounting frame 7 is detachably mounted on an end of the wheelchair frame body 1 away from the driving rear wheel 2 and located under the seat cushion 4, a pedal gear 8 is rotatably mounted at a bottom of the mounting frame 7 and a pedal 801 is provided on the pedal gear, and a hand crank gear 9 is rotatably mounted on a top of the mounting frame 7 and a hand crank handle 901 is provided on the hand crank gear 9. A rotating shaft is provided between two driving rear wheels 2 and rotatably mounted on the wheelchair frame body 1, two driving rear wheels 2 are fixedly mounted on both ends of the rotating shaft, respectively, and a driven gear 10 is fixedly mounted on the rotating shaft. A supporting chain gear 11 is rotatably mounted on the mounting frame 7 and arranged adjacent to the pedal gear 8. The hand crank gear 9, the pedal gear 8, the driven gear 10 and the supporting chain gear 11 are wound by a transmission chain 12, the transmission chain 12, the hand crank gear 9, the pedal gear 8, the driven gear 10 and a steering gear are arranged in an engagement arrangement, and the hand crank gear 9, the pedal gear 8, the driven gear 10 and the supporting chain gear 11 are connected and driven by the transmission chain 12. Through the hand crank handle 901 and the pedal 801, while embodying the exercise of hands and feet, the wheelchair can be driven at the same time to meet the needs of exercise and autonomous walking.

In this embodiment, one end of the mounting frame 7 is fixedly mounted on the wheelchair frame body 1 through the mounting plate and using bolts, and the mounting is firm and easy to disassemble.

In this embodiment, in order to make the driving of the wheelchair more labor-saving, the gear outer diameter of the pedal gear 8 and the hand crank gear 9 is larger than the gear outer diameter of the driven gear 10.

A protective shell 13 is also fixedly mounted on the mounting frame 7. The protective shell 13 is arranged to cover the hand crank gear 9, the pedal gear 8 and the supporting chain gear 11. The provided protective shell 13 plays a role in protecting the user, preventing the user from being scratched by gears and chains and getting clothes dirty during exercise. At the same time, it also protects the gears and chains, effectively avoiding the entry of dust, impurities, etc., so that the service life is greatly extended, and the appearance of the wheelchair is more beautiful.

The seat cushion 4 and the backrest 5 are provided with a massage cushion 14, and the massage cushion 14 is located below surface layers of the seat cushion 4 and the backrest 5. In this embodiment, the massage cushion 14 can be directly used as a commercially available product, which is agreed by those skilled in the art. Therefore, it will not be repeated here. The provided massage cushion 14 has the function of physiotherapy and massage on the user's back, waist, buttocks and thighs. The physiotherapy massage provided by the massage cushion 14 can promote blood circulation and unblocked meridian, thereby greatly improving the effect of the user's rehabilitation exercise.

An iontophoresis instrument 15 is fixedly mounted on a back of the backrest 5, and an electrode plate 16 connected to the iontophoresis instrument 15 is detachably mounted on a leaning surface of the backrest 5. The leaning surface of the backrest 5 is also equipped with a medicine bag 17 for holding medicine packs. The medicine bag 17 and the electrode plate 16 are arranged correspondingly. In this embodiment, the iontophoresis instrument 15 can be a commercially available digital controlled frequency modulation pulse therapeutic instrument, which will not be repeated here. When in use, the required medicine packet is put into the medicine bag 17. Under the action of the iontophoresis instrument 15, the electrode plate 16 and the medicine packet are combined to generate a directional driving force on the medicine ions, so that the effective ingredients in the medicine can penetrate the skin and mucous membranes and quickly enter the human body, acting on the user to embody the physical therapy and treatment functions of the user's treatment place, which is more conducive to the user's rehabilitation effect.

In this embodiment, in order to embody the installation of the electrode plate 16 on the backrest 5, the electrode plate 16 is fixedly mounted on the backrest 5 by Velcro, which is not only convenient for disassembly and assembly, convenient for maintenance and replacement, but also enables fine adjustment of the installation position.

In this embodiment, the medicine bag 17 is a hollow mesh bag, and the hollow mesh bag-type medicine bag 17 facilitates the taking and placing of the medicine packet, and at the same time, it is more convenient for the medicine packet to act on the user, and the treatment effect is better.

A vital signs detector 18 is also fixedly mounted on the back of the backrest 5. The vital signs detector 18 is connected with an electrode sheet 19, and a storage box for placing the electrode sheet 19 and connecting wires can be arranged in the vital signs detector 18. The vital signs detector 18 facilitates the detection of the user's vital signs such as blood pressure, blood lipids, blood sugar and other vital signs, so as to embody the effective monitoring of the user's vital signs, thereby helping to adjust the signs of exceeding the standard in time. By sticking the electrode sheet 19 on the user's temples and other acupuncture points, it also has physical therapy and the prevention and treatment of cerebrovascular diseases. Since the vital signs detector 18 is existing relatively mature medical testing equipment, which is agreed by those skilled in the art, it will not be repeated here.

An oxygen generator 20 is fixedly mounted at a bottom of the seat cushion 4. In this embodiment, the oxygen generator 20 may be a commercially available oxygen generator and atomization integrated machine with a negative oxygen ion function. The oxygen concentrator 20 is equipped with independent oxygen inhalation tubes and masks, which is convenient for users with impaired respiratory system to inhale at any time, especially during exercise, which is of great help to the elderly and users with impaired respiratory system. The effect is to improve brain hypoxia and insufficient blood supply, which can reduce the difficulty of exercise for users, so as to meet the needs of the elderly and users with impaired respiratory system to exercise, achieve the required amount of exercise, and achieve better rehabilitation effects.

One armrest of the wheelchair frame 1 is provided with a receiving box 21, and the other armrest is provided with a display screen 22. The provided display screen 22 can embody the display of the user's health information and facilitate the user to understand the health information. The exercise plan displayed on the display screen 22 is also more convenient for the user to carry out the exercise of the corresponding rehabilitation item in a reasonable and planned manner, which is convenient and practical. In this embodiment, the display screen 22 can be provided with a USB interface for connection, and can also be added to the display screen 22 with music playback, weather broadcast, simple voice dialogue, and other currently relatively mature intelligent system functions (such as the existing vehicle display screen 22) to increase the convenience of using the exercise chair.

Certainly, the multifunctional exercise chair for body stretching is also equipped with a power source to provide power for the massage cushion 14, the iontophoresis instrument 15, the vital signs detector 18, the oxygen generator 20, and the display screen 22. The power source can be a battery, which is mounted on the wheelchair frame body 1 under the seat.

In addition to the above-mentioned structure and function, the multifunctional exercise chair for body stretching in this embodiment has other exercise structures with the same function as the Chinese invention patent with the patent number CN201910277129.X of which title of the invention is multifunctional wheelchair with restoration function, and other details are not repeated here.

Based on the above structure, the multifunctional exercise chair for body stretching has various functions. While embodying the mobility function for the physically disabled and the disabled, the present disclosure also has the exercise function, which is convenient for the user to perform rehabilitation exercises, so as to avoid physical function degradation and resume daily life and the purpose of self-care ability, and at the same time exercise the hands and feet through the hand crank handle 901 and pedal 801, thereby embodying the driving of the wheelchair and autonomous walking.

The elderly, especially those with limited mobility, are most afraid of accelerated aging, various chronic diseases, lack of freedom of movement, lack of companionship, inability to exercise, weight gain, inability to do outdoor activities, inability to enjoy the sun indoors, and unpresentable to the public, so that they are far away from the pain, loneliness, depression and sadness caused by many disability problems such as society and nature. However, aging, pessimism, loss of the meaning of life, and the root causes of the torture of various diseases are caused by the decline of instinct. The decline of human and physical instincts is the result of a long-term disability. When the instinct declines, people's confidence, yearning for a better life in the future, dreams and desires, and behavior activities will gradually become less and less satisfactory. People will reduce or relax their muscles, tendons and tendons to become shorter due to less and less exercise in walking. In addition, they will inevitably be accompanied by the decline in the functions of the brain, heart, lungs, and internal organs, various psychological problems, aging problems and a series of chronic diseases gradually aggravated or occurred.

There is a vitality instinct for a muscle, and the muscles are longer than an inch for more than ten years. This model is designed for the elderly and people with disabilities to exercise and stretch muscles and provide energy and various lifestyle AI rehabilitation experts, AI speakers, cardiopulmonary monitoring and other multi-service multi-function chairs, which is the infinite love for the elderly. The data proves that one day the elderly will not be able to move independently and safely because they want to move. People will experience a slow, long-lasting pain in bed due to a fall, and the proportion of their lives taken in the end is increasing. This equipment starts with a combination of aerobic and energy supply and accompanied by beautiful music to exercise the muscles of various parts of the body and stretch various tendons. The principle is to stimulate the instinct of the living body, so that the instinct of the body will increase muscles and tendons in order to adapt to this kind of external artificial stimulation. This is not only the rapid improvement of osteoporosis in many elderly people who have no obvious effect of calcium supplementation. This process is actually a process of enhancing instinct, and also includes negative oxygen ions and oxygen energy generators and the designed AI rejuvenation. The joint function of the expert system and the coordinated guidance of body, mind, life style rehabilitation and music will quickly enhance instinct.

Once the instincts of humans and living bodies are stimulated and improved, the vitality of life's body, mind, and various organ systems will increase, their functions will be enhanced, and the state of life will be completely improved. Consequently, it is significantly beneficial to slow down aging, prevent chronic diseases, stroke and dementia, improve cardiopulmonary function and allow the elderly to live a happy old age.

The multifunctional exercise chair for body stretching of the present disclosure that exercises muscles, stretches muscles, provides various energy, and can more fully provide the function of outdoor free activities, chatting with people and integrating into nature, is an inseparable life partner and life support for the elderly. The fundamental difference between the present disclosure and the electric chair on the market is that people stay on the conventional electric chair forever and wait for the instinct to drop continuously, gain weight and gradually lose their various abilities while being plagued by various diseases; however, the multifunctional exercise chair for body stretching of the present disclosure is to enhance the instinct, the body, mind, and soul are fully renewed, so that the quality of life is improved to make life full of vitality.

It should be understood that the purpose of these embodiments is only to illustrate the present disclosure and is not intended to limit the protection scope of the present disclosure. In addition, it should also be understood that after reading the technical content of the present disclosure, those skilled in the art can make various changes, modifications and/or modifications to the present disclosure, and all these equivalent forms also fall into the appended claims of this application. Within the limited scope of protection.

What is claimed is:

1. A multifunctional exercise chair for body stretching, comprising a wheelchair frame body on which driving rear wheels, steering front wheels, a seat cushion, a backrest and a hand-pushing armrest are mounted, wherein a mounting frame is detachably mounted on an end of the wheelchair frame body away from the driving rear wheel and located under the seat cushion, a pedal gear is rotatably mounted at a bottom of the mounting frame and a pedal is provided on the pedal gear, and a hand crank gear is rotatably mounted on a top of the mounting frame and a hand crank handle is provided on the hand crank gear;

a rotating shaft provided between two driving rear wheels and rotatably mounted on the wheelchair frame body, two driving rear wheels fixedly mounted on both ends of the rotating shaft, respectively, and a driven gear fixedly mounted on the rotating shaft;

a supporting chain gear rotatably mounted on the mounting frame and arranged adjacent to the pedal gear; and the hand crank gear, the pedal gear, the driven gear and the supporting chain gear wound and connected by a transmission chain;

wherein the seat cushion and the backrest are provided with a massage cushion and the massage cushion is located below surface layers of the seat cushion and the backrest;

wherein an iontophoresis instrument is fixedly mounted on a back of the backrest, and an electrode plate connected to the iontophoresis instrument is detachably mounted on a leaning surface of the backrest; and the leaning surface of the backrest is further equipped with a medicine bag for containing medicine packets, and the medicine bag is arranged corresponding to the electrode plate.

2. The multifunctional exercise chair for body stretching according to claim 1, wherein a protective shell is further fixedly mounted on the mounting frame and arranged to cover the hand crank gear, the pedal gear and the supporting chain gear.

3. The multifunctional exercise chair for body stretching according to claim 1, wherein the electrode plate is fixedly mounted on the backrest through Velcro.

4. The multifunctional exercise chair for body stretching according to claim 3, wherein the medicine bag is a hollow mesh bag.

5. The multifunctional exercise chair for body stretching according to claim 1, wherein a vital signs detector is further fixedly mounted on the back of the backrest and connected with an electrode sheet.

6. The multifunctional exercise chair for body stretching according to claim 5, wherein an oxygen generator is fixedly mounted at a bottom of the seat cushion.

7. The multifunctional exercise chair for body stretching according to claim 6, wherein a receiving box is arranged on one of hand-pushing armrests of the wheelchair frame body, and a display screen is arranged on the other one of the hand-pushing armrests.

\* \* \* \* \*